US00RE36601E

United States Patent [19]

Woods et al.

[11] E Patent Number: Re. 36,601

[45] Reissued Date of Patent: Mar. 7, 2000

[54] METHOD FOR MAKING MULTILAYER PAD

[75] Inventors: James M. Woods; Marilyn S. Woods, both of Pisgah Forest, N.C.

[73] Assignee: M.J. Woods, Inc., Hendersonville, N.C.

[21] Appl. No.: 09/059,479

[22] Filed: Apr. 13, 1998

Related U.S. Patent Documents

Reissue of:

[64] Patent No.: 5,507,906
Issued: Apr. 16, 1996
Appl. No.: 08/285,183
Filed: Aug. 3, 1994

U.S. Applications:

[63] Continuation of application No. 08/097,274, Jul. 26, 1993, abandoned, which is a continuation-in-part of application No. 07/954,688, Sep. 30, 1992, Pat. No. 5,230,119, which is a continuation of application No. 07/684,593, Apr. 12, 1991, abandoned, which is a continuation-in-part of application No. 07/508,967, Apr. 13, 1990, abandoned.

[51] Int. Cl.[7] ..... B32B 31/12; B32B 31/18

[52] U.S. Cl. ..... 156/271; 156/250; 156/268; 156/269; 156/291; 156/324; 156/548; 156/578; 15/209.1

[58] Field of Search ..... 156/250, 268, 156/269, 270, 290, 291, 320, 324, 548, 578; 15/209.1

[56] References Cited

U.S. PATENT DOCUMENTS

| | | |
|---|---|---|
| Re. 26,385 | 5/1968 | Gilchrist . |
| 1,893,523 | 1/1933 | Radzinsky . |
| 1,950,840 | 3/1934 | Cook . |
| 1,957,016 | 9/1934 | Nassif . |
| 2,156,270 | 5/1939 | Smith . |
| 2,237,346 | 4/1941 | Gilfillan . |
| 2,382,930 | 8/1945 | Williams . |
| 2,616,428 | 11/1952 | Magee . |
| 2,629,890 | 3/1953 | Giovanna . |
| 2,653,888 | 9/1953 | Hyman, Jr. . |
| 2,841,811 | 7/1958 | Carroll . |
| 2,927,335 | 3/1960 | Hammond . |

(List continued on next page.)

FOREIGN PATENT DOCUMENTS

| | | |
|---|---|---|
| 607525 | 7/1926 | France . |
| 660938 | 7/1929 | France . |
| 582504 | 12/1976 | Switzerland . |
| 4609 | of 1915 | United Kingdom . |
| 6160 | 3/1916 | United Kingdom . |
| 1158412 | 7/1969 | United Kingdom . |
| 95/03175 | 2/1995 | WIPO . |

OTHER PUBLICATIONS

Dia 112 from "Coating and Laminating Machines" by Herbert L. Weiss, Converting Technology Company, Milwaukee, WI 53211 (1983).

"Dry Bonding" and "Wet Bonding" from Morton Chemical Adhesives and Coatings Handbook.

Booklet published by Kimberly–Clark regarding KIMDURA® Synthetic Paper.

"Accuracy, Consistency, Profit Boost Popularity of Gravure" by Herbert Weiss, Paper, Film & Foil Converter, Apr. 1992.

International Application No. PCT/US 91/02525, as published as No. WO 91/15983 on Oct. 31, 1991.

*Primary Examiner*—Curtis Mayes

[57] ABSTRACT

The invention comprises a method for manufacturing a laminated pad in a cost-efficient manner. In one embodiment, the method comprises the steps of applying strips of adhesive to a first substrate and mounting the first substrate to a second substrate. Next, adhesive is applied to the entire width of a third substrate which is in turn mounted to the laminated first and second substrates to create a laminated sheet. The laminated sheet can be slit and then die cut into individual laminated pads. The pads which result from this process have a base pad, an intermediate layer which is adhered to the base pad and a top layer in which only a portion of the top layer is mounted to the intermediate layer.

7 Claims, 12 Drawing Sheets

U.S. PATENT DOCUMENTS

| | | |
|---|---|---|
| 2,961,677 | 11/1960 | Zecchini . |
| 2,964,772 | 12/1960 | Crawford . |
| 2,975,453 | 3/1961 | Imhof . |
| 3,104,915 | 9/1963 | Perkovich et al. . |
| 3,131,410 | 5/1964 | Anderson et al. . |
| 3,142,855 | 8/1964 | Gilchrist . |
| 3,221,359 | 12/1965 | Moroni et al. . |
| 3,236,713 | 2/1966 | Taff . |
| 3,369,267 | 2/1968 | Friedland et al. . |
| 3,638,270 | 2/1972 | Schlegal, Jr. et al. . |
| 3,666,611 | 5/1972 | Joa . |
| 3,694,845 | 10/1972 | Engelsher . |
| 3,737,939 | 6/1973 | Jones, Sr. . |
| 3,784,998 | 1/1974 | Jones, Sr. . |
| 3,843,991 | 10/1974 | Vallis . |
| 3,955,233 | 5/1976 | Nakamura . |
| 4,014,616 | 3/1977 | Mast, Jr. et al. . |
| 4,053,242 | 10/1977 | Mast, Jr. . |
| 4,121,386 | 10/1978 | Perez . |
| 4,203,857 | 5/1980 | Dugan . |
| 4,342,613 | 8/1982 | O'Leary et al. . |
| 4,372,867 | 2/1983 | Taragos . |
| 4,506,404 | 3/1985 | Clay . |
| 4,562,099 | 12/1985 | Hinchcliffe . |
| 4,684,433 | 8/1987 | Gohr . |
| 4,701,168 | 10/1987 | Gammons . |
| 4,829,995 | 5/1989 | Metters . |
| 4,893,956 | 1/1990 | Wojcik et al. . |
| 4,925,453 | 5/1990 | Kannankeril . |
| 5,230,119 | 7/1993 | Woods et al. . |
| 5,771,524 | 6/1998 | Woods et al. ..... 15/209.1 |

METHOD FOR MAKING MULTILAYER PAD

Matter enclosed in heavy brackets [ ] appears in the original patent but forms no part of this reissue specification; matter printed in italics indicates the additions made by reissue.

CROSS-REFERENCE TO RELATED APPLICATIONS

This is a continuation of application Ser. No. 08/097,274 filed Jul. 26, 1993, now [abandoned. Now], which is a continuation-in-part of U.S. patent application Ser. No. 07/954,688, filed Sep. 30, [1991,] *1992*, now issued as U.S. Pat. No. 5,230,119, which is a continuation of U.S. patent application Ser. No. 07/684,593, filed Apr. 12, 1991, now abandoned, which was a continuation-in-part of U.S. patent application Ser. No. 07/508,967, filed Apr. 13, 1990, now abandoned.

FIELD OF THE INVENTION

The present invention relates to a method of making a disposable multilayer pad. In particular, the present invention relates to a method for making an improved hand held laminated pad suitable as a wipe and/or applicator. The laminated pad has a base pad, an impervious barrier shield that protects the user from contact with fluids and solids on the base pad and a flexible, adjustable handle.

BACKGROUND OF THE INVENTION

Many items are widely used as wipes and applicators for wiping or applying substances from or to surfaces such as those on a human, e.g., skin, finger nails, toe nails, or in a human, e.g., internal organs and bones during a surgical operation. These items are widely used in both medical and non-medical fields. Small cotton or rayon balls, pads or gauzes are perhaps the most widely used items for these purposes on the market today. Small sponges are also widely used items.

In the medical field, these items are used for cleaning the skin and other surfaces, such as the surfaces of internal organs, by the application of a disinfectant or solvent and/or the wiping away of blood and other fluids, including other body fluids, and other materials. The cotton balls, sponges and gauze pads are grasped between the fingers and applied to the area of concern to wipe away or apply fluids or other materials. One problem with this prior art approach is that the fingers can easily come into contact with the fluid being applied or wiped. In light of infectious diseases such as AIDS and hepatitis contact between a care provider and a patient should be avoided.

In the cosmetics and personal care fields, cotton balls and the like are widely used to apply and to remove makeup and to apply other personal care products such as lotions, creams and nail polish remover. Unfortunately, the item transfers the makeup or personal came product to the user's finger which is often undesirable. For example, when a nail polish remover, which is usually acetone or acetate based, is being used it can be transferred to the fingers of the hand holding the item. The nail polish remover can harm the fingers and remove the nail polish from the user's finger nails on the hand holding the item even if removal from these nails was not desired. Also, the nail polish remover can undesirably remove nail polish from a finger nail adjacent to the finger from which the nail polish is being removed. Also, the transfer can result in a waste of the makeup or personal care product.

These items are often amorphous in that they have no defined shape and therefore no defined edges. Thus, these items are not ideally suited to apply or wipe materials to or from surfaces that have an arcuate edge, e.g., finger nails, and from surfaces that have straight edges, e.g., the edge formed between the nose and cheek. Other items only have arcuate or straight edges and are not very effective when surfaces having a different shape are encountered.

One example of the prior art approach is disclosed in U.S. Pat. No. 4,053,242, entitled "Disposable Product Applicator and Dispensing Package Therefor", issued Oct. 11, 1977 to Mast, Jr. Another example of applicators is illustrated in the Jones, Sr. U.S. Pat. No. 3,784,998, entitled "Composition Applicator" and its companion case U.S. Pat. No. 3,737,939 having substantially identical disclosures. Other prior attempts include U.S. Pat. No. Re. 26,385, to Gilchrist issued May 7, 1968, which discloses a liquid and paste applicator formed by sheets of foam; and U.S. Pat. No. 4,506,404 to Clay which discloses a disposable sponge having a planar body portion and a pair of upstanding rib members spaced close enough that they may be grasped and squeezed against each other by the hand to form a handle or grip.

It is desirable to manufacture an improved laminated pad suitable for use as an applicator or wipe that overcomes at least some of the aforementioned shortcomings in a cost effective manner.

SUMMARY OF THE INVENTION

The invention comprises a method of manufacturing a multilayer pad comprising the steps of providing a base pad forming material having an attachment surface and an application surface, providing an intermediate layer forming material having an upper attachment surface and a lower attachment surface, and providing a handle forming material having a lower attachment surface and an exposed upper surface. The attachment surface of the base pad forming material is mounted to the lower attachment surface of the intermediate layer forming material such that substantially the entire lower attachment surface of the intermediate layer forming material is mounted to the upper attachment surface of the base forming material. A portion of the upper attachment surface of the intermediate layer forming material is mounted to the lower attachment surface of the handle forming material such that less than the entire upper attachment surface of the intermediate layer forming material is mounted to the lower attachment surface of the handle forming material. Finally, the laminated sheet is cut into individual pads having a mounted portion of the handle forming material and a pivotable portion of the handle forming material.

Preferably, the base pad material is mounted to the intermediate layer by adhesive which is applied by a cylinder having a plurality of recesses formed therein adapted to transfer adhesive from a reservoir to the material.

In another embodiment, the intermediate layer forming sheet is mounted to the handle forming sheet by adhesive which is applied in strips parallel to one another. Preferably, the parallel strips are applied to one of the intermediate layer forming sheet and the handle forming sheet by rolling one of the sheets over a zone cylinder adapted to apply adhesive to the sheet in the parallel strips.

In another embodiment, the method comprising the step of cutting the laminated sheet such that the mounted portion of two adjacent pads are cut from the same strip of adhesive coating of the laminated sheet.

In a further embodiment, the method comprises the step of cutting the sheet such that the pivotable portion of two adjacent pads are cut from the same strip of uncoated portions of the sheet.

In a further embodiment of the invention, the several layers are bonded to one another by co-extrusion of the several layers and passing the layers between a pair of opposed rolls immediately after extrusion such that the several layers are bonded to one another.

DETAILED DESCRIPTION OF A PREFERRED EMBODIMENT

Figure 1:
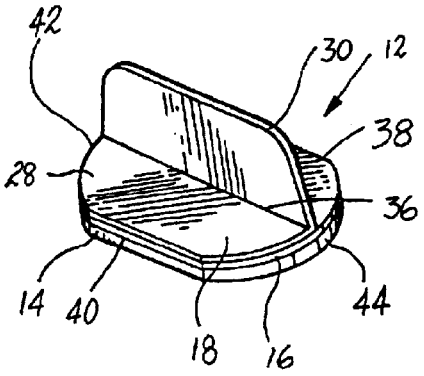
FIG. 1 is a perspective view of a first embodiment of the laminated pad manufactured according to the invention.
Figure 2:
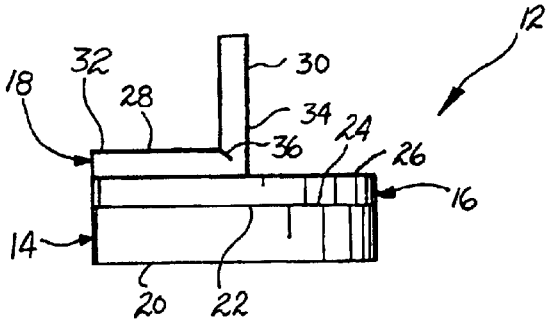
FIG. 2 is a front elevation view of the laminated pad of FIG. 1.

Referring to the drawings, and to FIGS. 1 and 2 in particular, a first embodiment 12 of a laminated pad produced according to the invention is illustrated. The pad 12 comprises a base pad 14, an intermediate layer or impervious shield 16 mounted to the base pad 14 and a handle forming layer 18 mounted to the impervious shield 16. The base pad 14 has an application surface 20 and an upper mounting surface 22 opposite the application surface 20. Similarly, the impervious shield 16 has a lower mounting surface 24 and an upper mounting surface 26. The lower mounting surface 24 of the impervious shield 16 is bonded to the upper mounting surface 22 of the base pad 14.

The handle forming layer 18 comprises an upper surface 32 and a lower surface 34. A portion of the lower surface 34 of the handle forming layer 18 is mounted to the upper mounting surface 26 of the impervious shield 16 to create a mounted portion 28 and a handle portion 30 pivotally mounted to the mounted portion 28 of the handle forming layer 18. Preferably, a score line 36 is formed on the upper surface 32 of the handle forming layer 18 along the junction between the handle portion 30 and the mounted portion 28. The score line 36 allows the handle portion 30 to freely pivot or rotate about the score line 36 relative to the mounting portion 28.

In the preferred embodiment, the pad 12 comprises a pair of opposed parallel edges 38, 40, and a pair of opposed arcuate edges 42, 44. In addition, the base pad 14, impervious shield 16 and handle forming layer 18 are coextensive with one another when the handle portion 30 of the second sheet is folded down, parallel to the base pad 14.

The shield 16 is preferably formed of a pliable material which is impervious to fluids and solids to which the base pad 14 is exposed. Therefore, as the user grasps the handle portion 30 with his fingers, his fingers will be protected from the fluid or solid material by the impervious shield 16. An example of a suitable material for the impervious shield is Kimdura™ manufactured by Kimberly-Clark of Roswell, Ga.

The impervious shield 16 and handle forming layer 18 can be made of the same material, such as a suitable impervious non-reactant material. The material is preferably flexible and has structural integrity such that it can be easily handled and yet support the base pad 14. The shield 16 and handle forming layer 18 preferably have a thickness of approximately 2.5 mils. Other suitable materials for the impervious shield 16 and handle 18 include a plastic film or paper coated or impregnated with a plastic such as polyethylene or polypropylene, and the like.

The base pad 14 can be formed of a variety of absorbent or abrasive materials depending on the particular application for the pad 12. For example, the pad can be made of a non-woven synthetic material, e.g. polyester, entangled cotton, woven fabric, dermabrasive, sanding materials, foam and the like. Preferably, the base pad is made of a non-woven material that is soft, pliable, and reversibly absorbent, that is, a dry pad is able to absorb liquid and a wet pad can be used to apply the solution to a surface. A lintless pad is suitable for most applications. Preferably, the base pad is approximately ⅛ inch in thickness.

Suitable mounting of the shield 16 to the base pad 14 and the shield 16 to the handle forming layer 18 can be accomplished by mechanical bonding between the materials through the use of adhesives or a co-extrusion process.

A conventional adhesive can be used to bind the several layers together provided that the adhesive has sufficient strength to bond the various laminated layers and which is substantially nonactive with the laminated materials. In addition, the adhesive should be resistant to the expected substances to which the laminated pad will be exposed during use. As described below, the adhesive can be mounted to the several laminated layers by a wet bonding, a dry bonding or a hot melt process.

Figure 3:
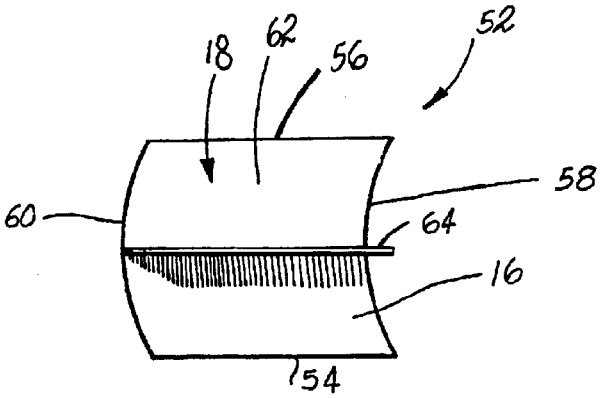
FIG. 3 is a top plan view of a second embodiment of the laminated pad manufactured according to the invention.
Figure 4:
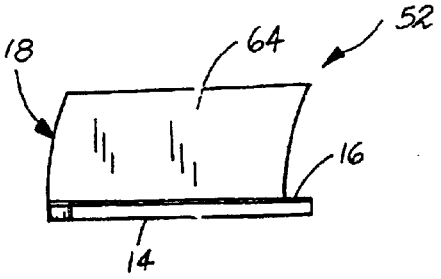
FIG. 4 is a side elevational view of the laminated pad of FIG. 3.

FIGS. 3 and 4 illustrate a second embodiment of the laminated pad 52 comprising the base pad 14, the impervious shield 16 and the handle forming layer 18 mounted thereto. The handle forming layer 18 has a mounted portion 62 and a handle portion 64. In this embodiment, the pad 52 has two parallel edges 54, 56, a concave arcuate edge 58 and a convex arcuate edge 60. The concave and convex edges 58, 60 can be utilized to enhance the cleaning or wiping performance of be pad on contoured surfaces.

Figure 5:
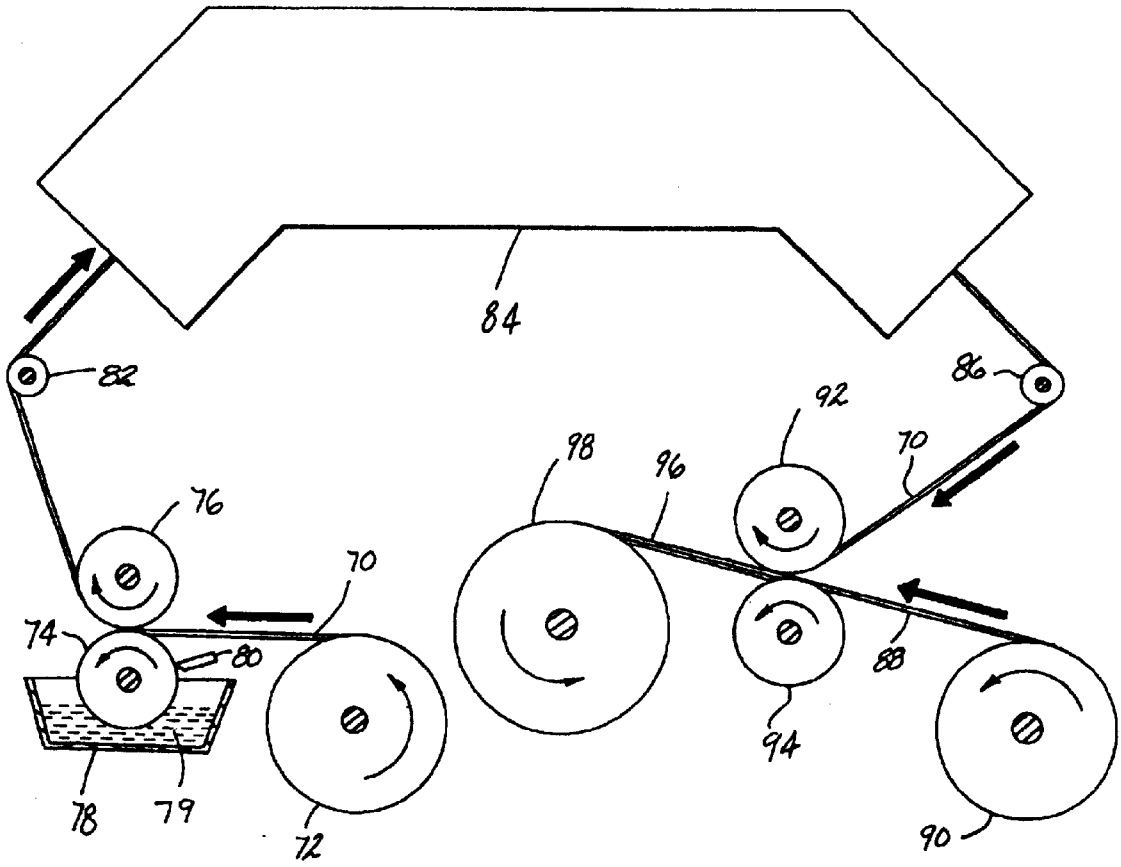
FIG. 5 is a schematic illustration of the first step of a first method of manufacturing the laminated pad according to the invention.

FIG. 5 is a schematic view of a portion of the first embodiment of the method for manufacturing the laminated pad 12 according to the invention and, more specifically, the method for adhering a sheet of handle material to a sheet of impervious shield material. A sheet of shield forming material 70 is supplied on a roll 72. The shield material sheet 70 is discharged from the roll 72 and passes between a zone forming gravure cylinder 74 and a rubber impression cylinder 76. The zone forming gravure cylinder 74 is in contact with a reservoir of liquid adhesive 78. As the gravure cylinder 74 rotates in the counterclockwise direction as seen in FIG. 5, adhesive adheres to the outer surface of the cylinder 74 and is ultimately applied to one side of the shield forming sheet 70 as it passes between the gravure cylinder 74 and the rubber impression cylinder 76. A doctor blade 80 is mounted between the liquid adhesive reservoir 73 and the junction between the zone forming gravure cylinder 74 and the rubber impression cylinder 76. The doctor blade 80 is mounted closely adjacent to or engages the zone forming gravure cylinder 74 to remove excess adhesive from the outer surface of the cylinder 74 to control the amount of adhesive applied to the sheet of shield forming material 70. Next, the shield forming material 70 engages a guide roller 82 and enters a drying tunnel 84 where heat is applied to the adhesive coated sheet 70. The sheet exits the drying tunnel 84 and engages yet another guide roller 86.

A sheet of handle forming material 88 is supplied on a roll 90 and engages the adhesive coated side of the shield forming sheet 70 between a pair of opposed nip rollers 92 and 94. The nip rollers 92, 94 apply a controlled amount of pressure to the shield forming sheet 70 and handle forming sheet 88 as the sheets pass between the two rollers 92, 94. The pressure applied by the rollers 92, 94 and the adhesive on the shield forming sheet 70 binds the two sheets together to create a laminated sheet 96. The laminated sheet 96 is stored on a roll 98 for further processing.

The adhesive can be applied by a wet bonding or dry bonding process. In the wet bonding process, the two sheets are combined while the adhesive is still wet. The adhesives are typically water-based proteins, starches, silicates, rubber lattices and resin emulsions. The wet bonding process is typically limited to applications in which one of the materials being laminated is porous enough to allow the adhesive solvent to escape. A dry bonding process is typically used with two non-porous materials. In this procedure, the adhesive is applied to one of the materials and the solvent is evaporated in the drying tunnel leaving behind the adhesive. The dry bonding process is typically used in laminating two non-porous materials such as the handle forming sheet 88 and the shield forming sheet 70.

Figure 6:
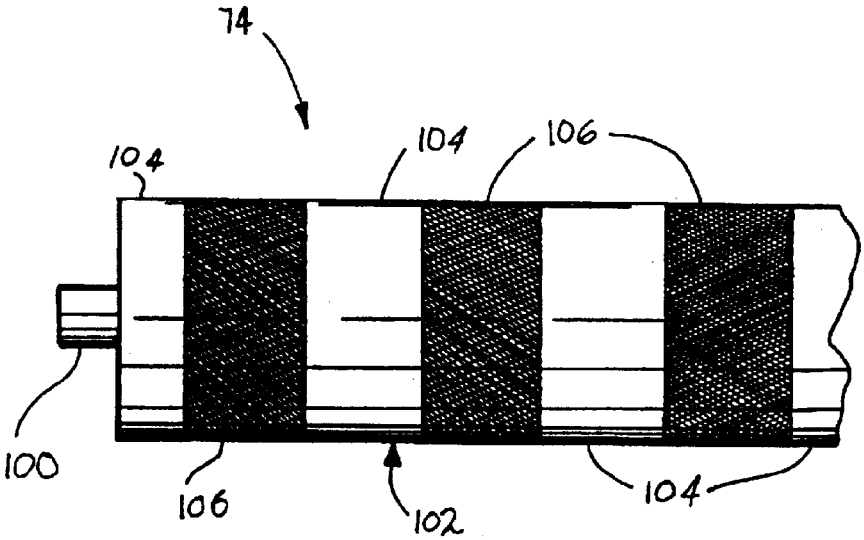
FIG. 6 is a front elevational view of a portion of a zone forming gravure cylinder for use in the first method of manufacturing a laminated pad according to the invention.
Figure 9:
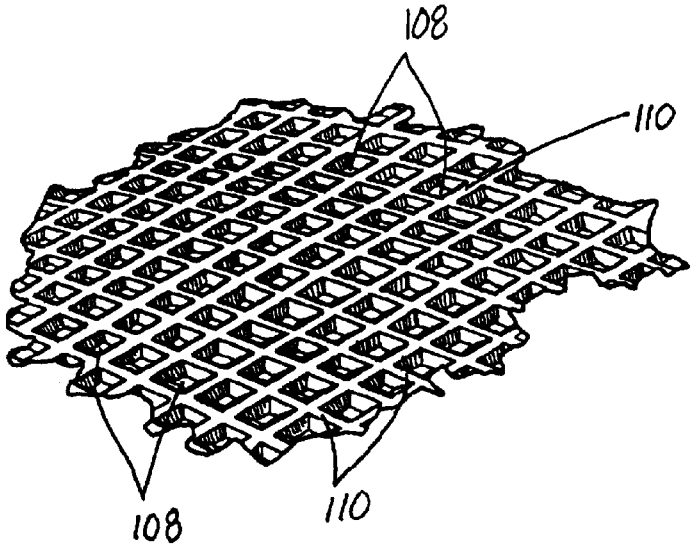
FIG. 9 is a close-up perspective view of the detents of the adhesive coating zone of the first embodiment of the gravure cylinder for use according to the invention.

As seen in FIG. 6, the zone forming gravure cylinder 74 comprises a support axle 100 and a tubular shaped body 102, which is divided into a plurality of smooth zones 104 and a plurality of gravure zones 106. The smooth zones 104 have a smooth outer surface with a diameter equal to the largest diameter of the tubular body 102. As seen in FIG. 9, the gravure zones 106 comprise an interlocking web of depressions or recesses 108 with smooth ribs no separating each of the recesses 108. The diameter of the rib portions 110 of the gravure zone 106 is substantially equal to the diameter of the smooth zones 104. However, the diameter of the recesses 108 of the gravure zone 106 is less than the diameter of the smooth zones 104 or ribs 110.

Figure 7:
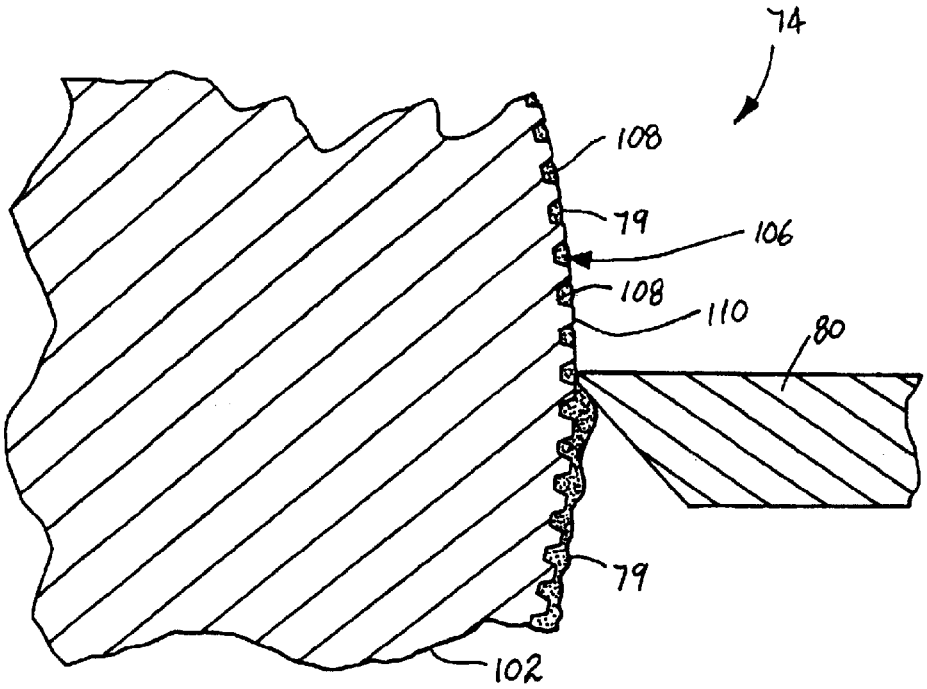
FIG. 7 is a partial sectional view of the adhesive coating zone, the zone forming gravure cylinder and doctor blade for use in the first method of manufacturing a laminated pad according to the invention.
Figure 8:
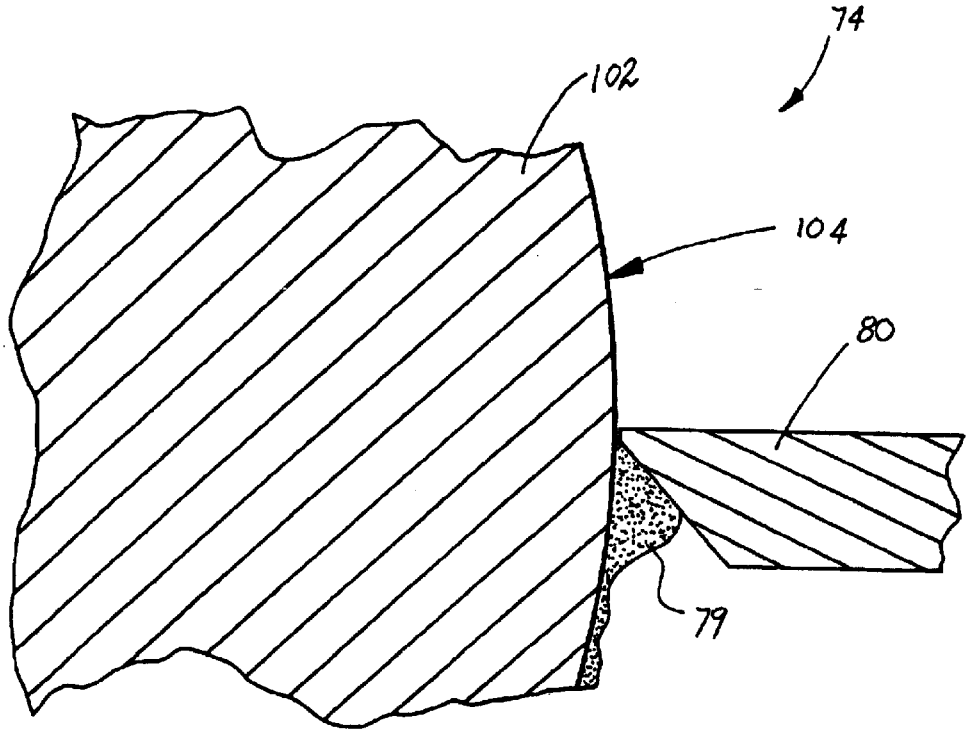
FIG. 8 is a partial sectional view of the zone forming gravure cylinder and doctor blade showing the no-coating zone for use in the first method of manufacturing a laminated pad according to the invention.

As seen in FIGS. 5, 7 and 8, the zone forming gravure cylinder 74 engages liquid adhesive 79 in the reservoir 78 and the adhesive 79 adheres to substantially the entire surface of the tubular body 102. As the cylinder 74 rotates, the adhesive encounters the doctor blade 80 which engages or is mounted closely adjacent to the outside surface of the tubular body 102. The doctor blade essentially scrapes or removes excess adhesive from the outer surface of the tubular body 102 of the cylinder 74. Preferably, the doctor blade 80 is adjusted to remove all adhesive from the smooth zones 104 and the ribs no of the gravure zones 106 while leaving adhesive within the recesses 108 of the gravure zones 106.

As the zone forming gravure cylinder 74 continues to rotate, the scraped surface of the tubular body 102 of the cylinder 74 engages one surface of the shield forming sheet 70. The adhesive contained within each of the several recesses 108 is transferred from the gravure zones 106 of the zone forming gravure cylinder 74 to one side of the shield forming sheet 70. In light of the removal of excess adhesive from the gravure zones 106, a bead-like pattern of adhesive will be applied to the shield forming sheet 70. In light of the alternating sequence of gravure zones 106 and smooth zones 104 along the length of the cylinder 74, a series of strips of adhesive material arm applied to the shield forming sheet 70. When the shield forming sheet 70 engages the handle forming sheet 88, only portions of the sheets corresponding to the strips of adhesive will be bonded to one another.

Figure 10:
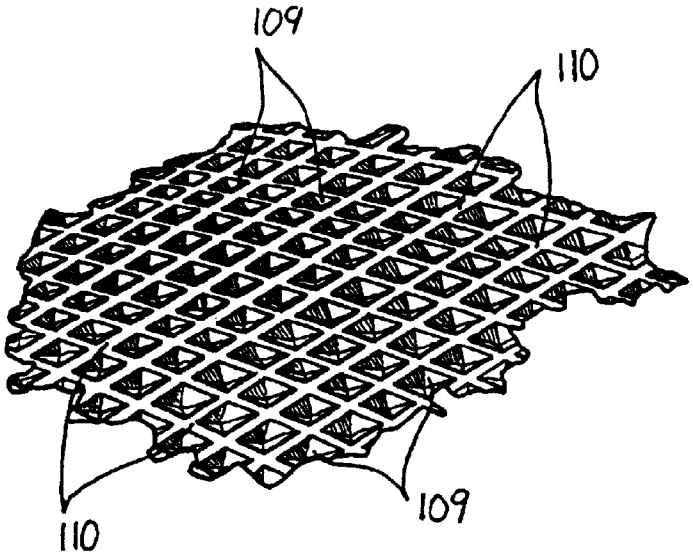
FIG. 10 is a close-up perspective view of the adhesive coating zone of a second embodiment of the detents of the gravure cylinder for use according to the invention.

As seen in FIG. 9, a first embodiment of the recess 108 is a truncated inverted pyramid. An alternative embodiment of the grave recesses 109, as seen in FIG. 10, comprises an inverted pyramid. The spacing between the gravure recesses and the relative depth of each of the recesses will determine the amount of adhesive which is applied to the sheet of material according to the process described above. The recesses are formed in the cylinder by a conventional mechanical incising, chemical etching or laser etching process.

White the embodiment described above provides for application of the adhesive to the top surface of the shield forming sheet, it is to be understood that the same process could be used to apply adhesive to the attachment surface of the handle forming sheet 88.

The laminated shield forming sheet 70 and handle forming sheet 88 can be mounted to the base forming material according to the same process as seen in FIG. 5. Namely, a roll of one of the base forming material or laminated sheet 96 engages an adhesive coated gravure cylinder, passes through a drying tunnel, and then is rolled into contact with the other of the base forming material or laminated sheet 96. However, in this step, a full gravure cylinder is used to apply adhesive to one of the base forming material or the laminated sheet 96.

Figure 11:
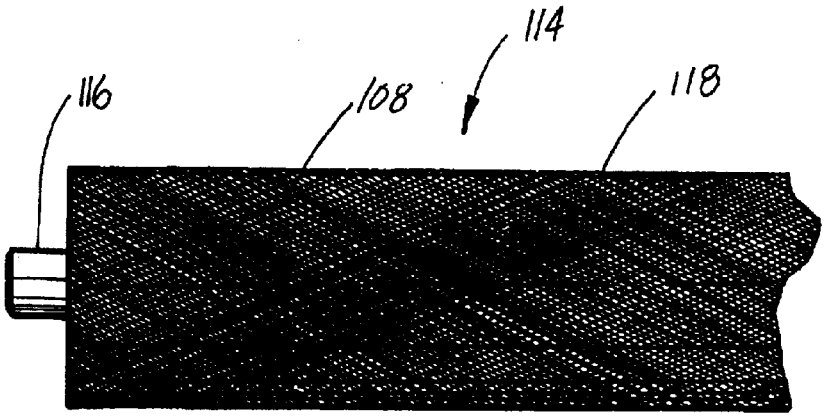
FIG. 11 is a front elevational view of a portion of the full gravure cylinder for use according to the invention.

As seen in FIG. 11, the full gravure cylinder 114 used to apply adhesive to one of the base forming material sheet or shield forming sheet comprises an axle 116, a tubular shaped body 118 having gravure recesses 108 formed on substantially the entire surface of the tubular shaped body 118. The gravure recesses 108 of the second gravure cylinder 114 are identical to the embodiments shown in FIGS. 9 and 10. As described above, the depth and spacing of the gravure recesses controls the amount of adhesive applied to the sheet. Preferably, a second doctor blade (not shown) is used to remove excessive adhesive from the cylinder 114 after the cylinder engages an adhesive reservoir.

Figure 12:
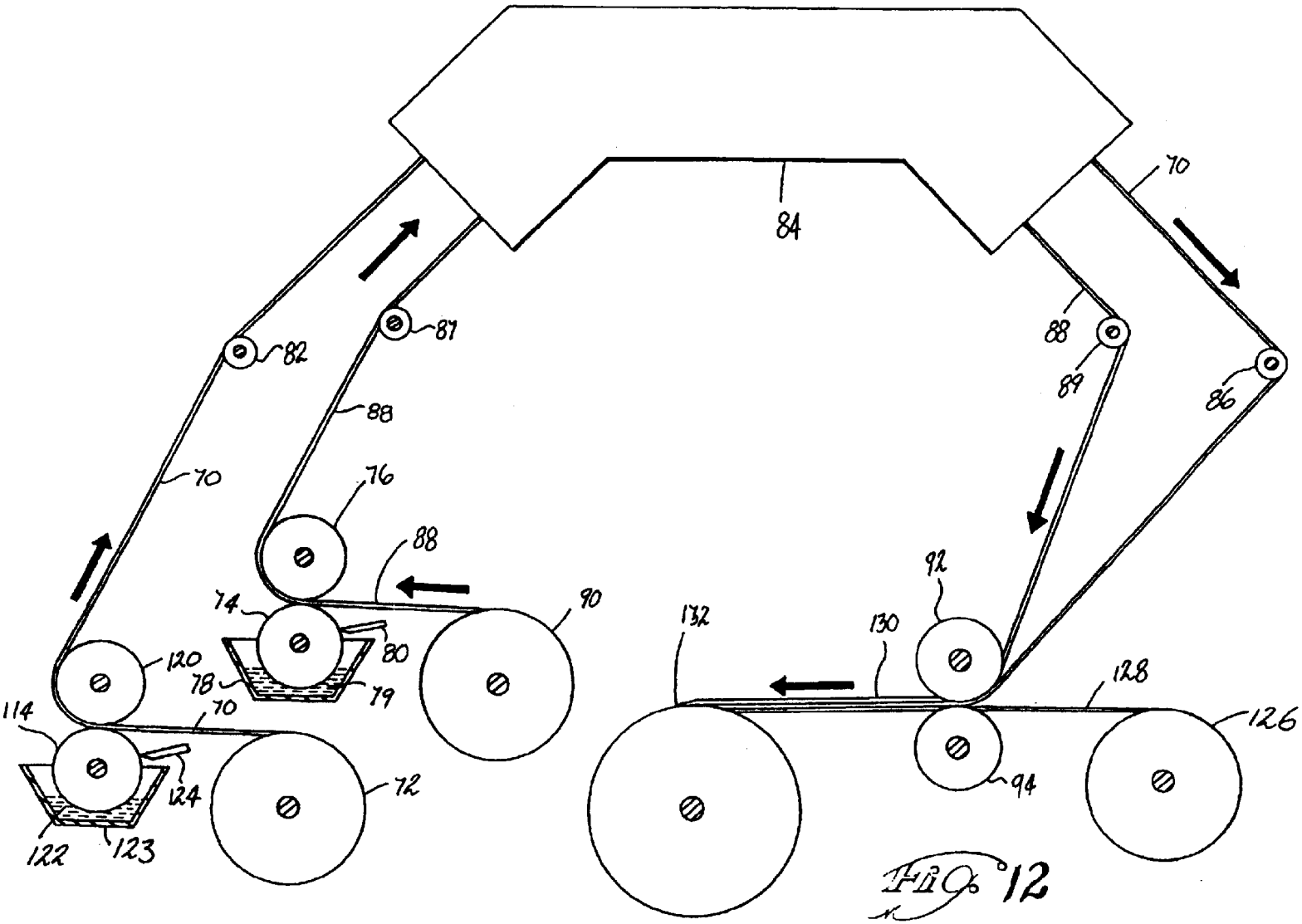
FIG. 12 is a schematic illustration of a portion of a second method of manufacturing the laminated pad according to the invention.

FIG. 12 shows a second method for manufacturing a laminated sheet from which the laminated pads 12, according to the invention, are cut. In this embodiment, a sheet of handle forming material 88 is discharged from the roll 90 and engages the zone forming gravure cylinder 74 and rubber impression cylinder 76. The adhesive 79 is supplied to the zone forming gravure cylinder 74 from the reservoir 78 and the excess adhesive is removed by the doctor blade 80. The adhesive coated sheet engages a guide roller 87 and passes through the drying tunnel 84 where it is subjected to heat. After exiting the drying tunnel 84, the adhesive coated sheet engages a guide roller 89.

The sheet of shield forming material 70 is supplied from a roll 72 and passes between the full gravure cylinder 114 and a rubber impression cylinder 120. The full gravure cylinder 114 applies adhesive to substantially the entire surface of one side of the shield forming material 70. The adhesive 122 is supplied to the full gravure cylinder from the reservoir 123 and the excess adhesive is removed by the doctor blade 124. Next, the sheet engages a guide roller 82 and enters the drying tunnel 84. The shield forming sheet 70 exits the drying tunnel and engages guide rollers 86. A sheet of base forming material 128 is supplied on a roll 126 and the shield forming sheet 70, handle forming sheet 88, and base material sheet in pass between the rubber roller 92 and master heated nip roller 94 to create the laminated sheet 130 which is stored on a roll 132 for future processing. Alternatively, the laminated sheet 130 can be transferred directly to a slitter 174 (FIG. 15) and then a die cutter 165 (FIG. 15) for slitting and cutting of the sheet into individual pads 12.

The second method for manufacturing the laminated sheet according to the invention can be modified by applying the adhesive from the full gravure cylinder 114 to the attachment surface of the base forming sheet 128 and by applying the zones of adhesive to the upper attachment surface of the shield forming sheet 70.

Figure 13:
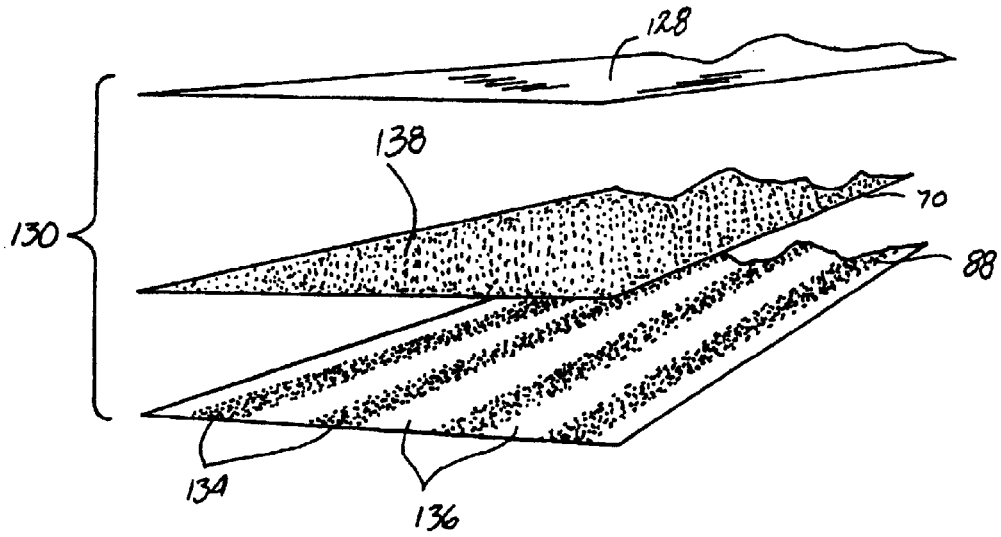
FIG. 13 is an exploded elevational view of the three sheets of material used to produce the laminated pad showing the adhesive coatings thereon.
Figure 14:
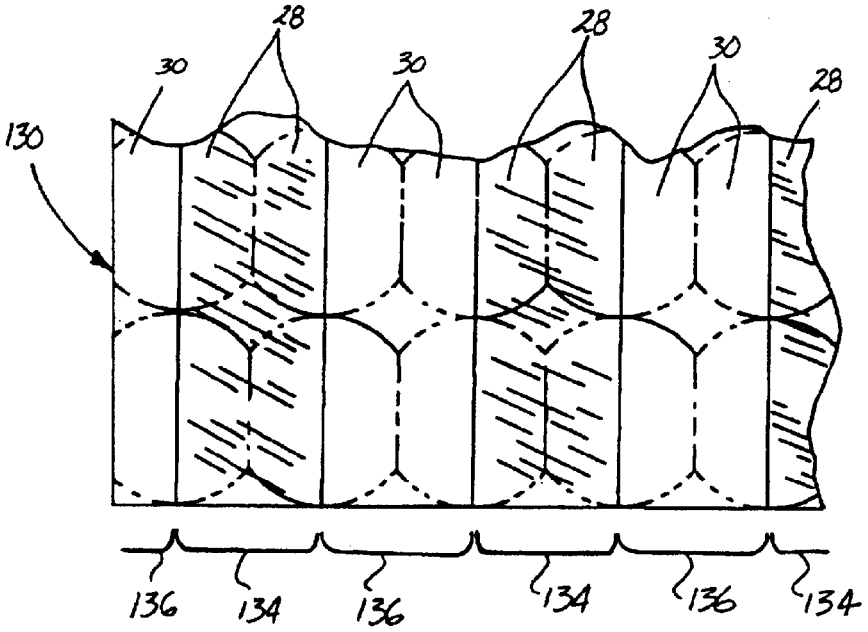
FIG. 14 is a top elevational view of the laminated sheet of material prior to cutting of the individual pads according to the invention showing the outline of the pads cut from the sheet in phantom lines and the alternating zones of adhesive.

As seen in FIG. 13, the laminated sheet 130 comprises the shield forming sheet 70 having adhesive 138 across substantially the entire surface, the handle forming sheet 88 having longitudinal strips of adhesive 134 separated by longitudinal strips of uncoated material 13 and the base forming sheet 128. The particular orientation and spacing of the strips of adhesive 134 and strips of uncoated material 136 becomes important when the laminated sheet is cut into the individual pads as seen in FIG. 14. This figure shows the outline of several pads 12 in phantom lines which are to be stamped from the laminated sheet 130 by a conventional die cutting operation. The strips of adhesive 134 and strips of uncoated material 136 are coordinated with the die cutting press to create the handle portion 30 and mounted portion 28 of each pad 12. Preferably, the strips of adhesive 134 are aligned such that two mounting portions 28 for two adjacent pads 12 are created from each strip of adhesive 134. In addition, each strip of uncoated material 136 is cut to create the handle portion 30 for two adjacent pads 12. Therefore, the strips of adhesive 134 and strips of uncoated material 136 are coordinated with the dies to create the handle portion and mounted portion of the handle forming sheet 88. After the laminated sheet 130 has been cut into individual pads, the pads can be packaged and in some cases sterilized for use by the end user.

The particular structure of the strips of adhesive 134 and strips of uncoated material 136 provide a significant advantage for the manufacturing method. Namely, if the sheet is slightly out of alignment with the cutting dies, then it is only the relative sizes of the handle portion or mounted portion of the adjacent pads which are affected. The pads will still be adequate for most purposes.

Figure 21:
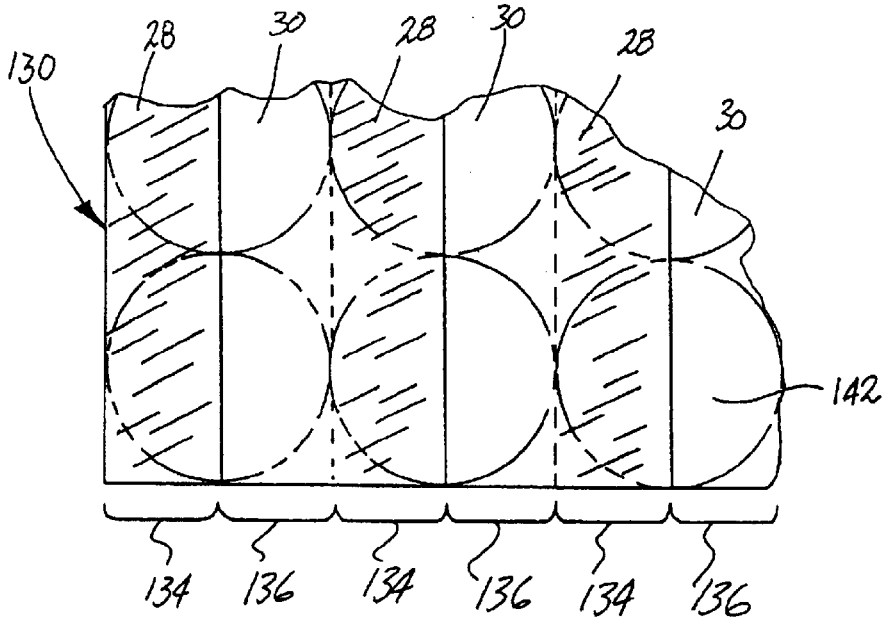
FIG. 21 is a top elevational view of the laminated sheet of material prior to cutting of the individual pads according to the invention showing the outline of the pads cut from the sheet in phantom lines and the alternating zones of adhesive.

Alternatively, the strips of adhesive 134 can be equal to the width of the mounted portion 28 of a single pad 12. In addition, the width of the uncoated portion 136 can be equal to the width of the handle portion 30 of a single pad 12. This configuration is depicted in FIG. 21. The pads 12 which are cut from the laminated sheet 130 are shown in phantom lines. FIG. 21 also depicts a third embodiment of the pads 142 in which the pads 142 are round and the outside perimeter of the base pad 14, impervious shield 16 and handle forming sheet 18 are co-extensive.

FIGS. 5–17 show a third embodiment of the method for producing a laminated pad 12 according to the invention. In this embodiment, the sheet of handle forming material 88 is supplied from a roll 90 and passes between a rubber impression cylinder 76 and a zone forming cylinder 150. The zone forming cylinder 10 picks up adhesive from the reservoir 152 and applies it to one side of the handle forming sheet 88.

The sheet of shield forming material 70 is supplied on roll 72 and passes between a rubber impression cylinder 154 and a full coating cylinder 156. The full coating cylinder 156 receives adhesive from a reservoir 158 and applies it to one side of the shield forming sheet 70.

The base forming sheet 128 is supplied on a roll 126. The base material 128, handle forming material 88 and shield forming material 70 pass simultaneously through a pair of opposed nip rollers 162, 164. The rollers 162, 164 apply pressure to the three sheets to create the laminated sheet 130. Next, the laminated sheet 130 is slit to an appropriate width for the die cutter 165. The slitter 174 comprises a support roller 175 and a circular slitting blade 176. Finally, the laminated sheet 130 passes to the die cutter 165 comprising a reciprocating cutter 167 and a mandrel 169 which cuts the individual pads from the laminated sheet 130.

Figures 15, 16, 17:
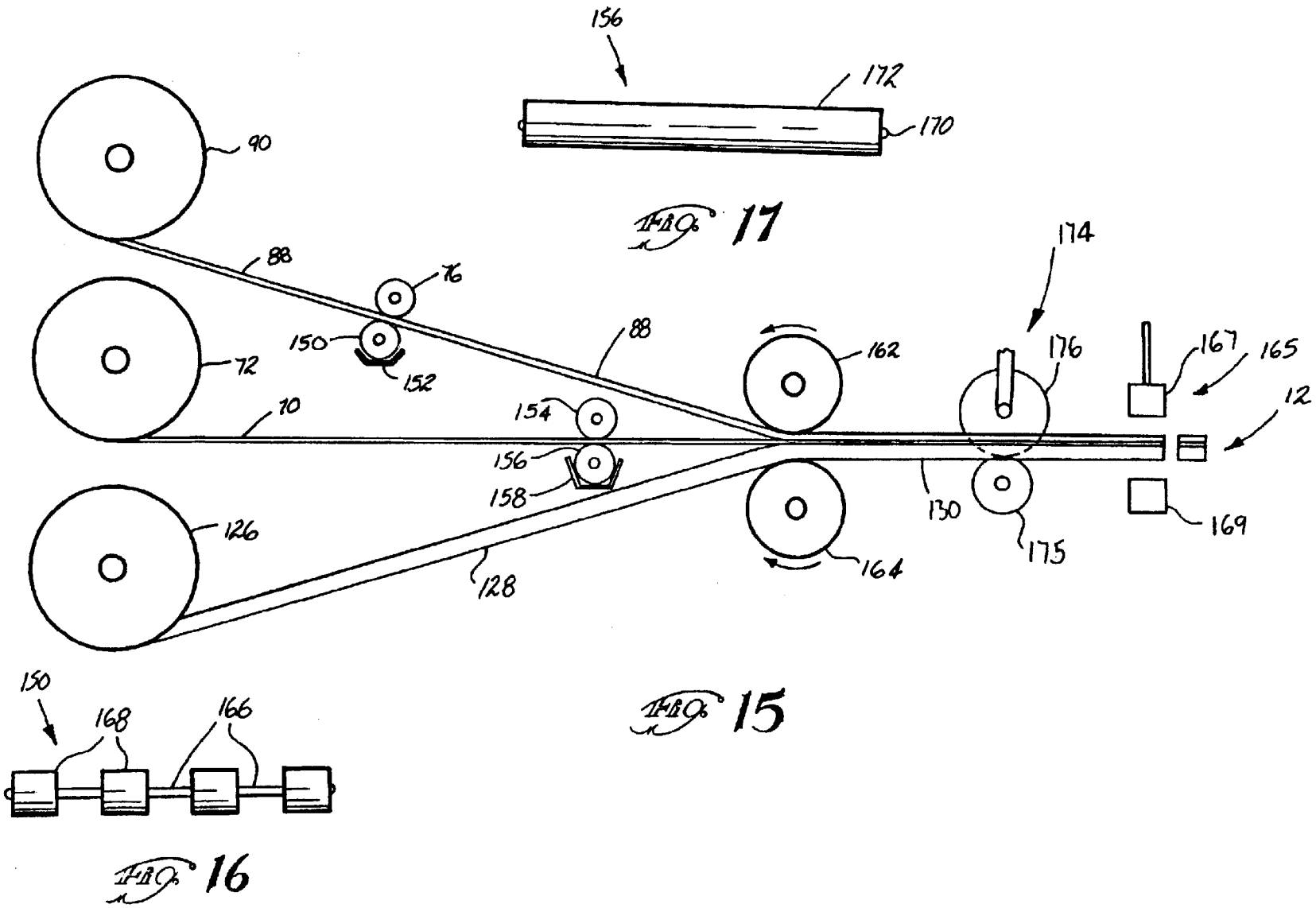
FIG. 15 is a schematic illustration of a third embodiment of a method for manufacturing a laminated pad according to the invention.
FIG. 16 is a front elevational view of a zone forming cylinder for use in the third method of manufacturing the laminated pad as seen in FIG. 15.
FIG. 17 is a front elevational view of an adhesive coating cylinder for use in the third method of manufacturing the laminated pad as seen in FIG. 15.

As seen in FIG. 16, the zone forming cylinder 150 of the third embodiment comprises an axle 166 and a plurality of adhesive coating sections 168. The adhesive coating sections 168 are spaced from one another and have a width which results in the creation of a laminated sheet with a plurality of strips of adhesive 134 and strips of uncoated material 136 as seen in FIGS. 13 and 14.

The full coating cylinder 156 of the third embodiment, as seen in FIG. 17 applies adhesive to substantially the entire surface of the sheet of shield forming material 70. The full coating cylinder 156 comprises an axle 170 and a tubular shaped body 172.

Figure 18:
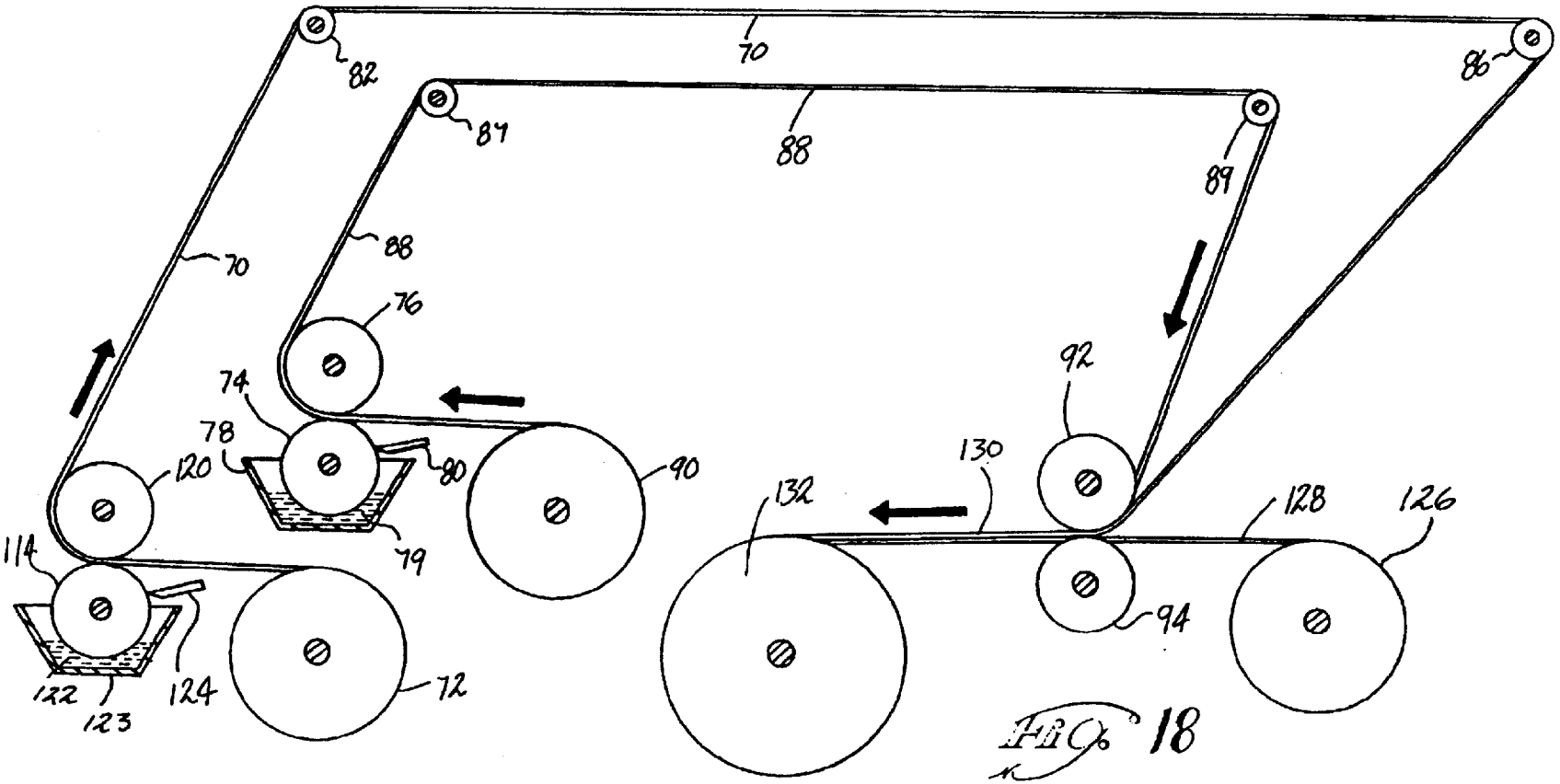
FIG. 18 is a schematic illustration of a fourth embodiment of a method for manufacturing the pad according to the invention.

A fourth embodiment of the method for manufacturing a laminated pad according to the invention is seen in FIG. 18. This method is identical to the third embodiment depicted in FIG. 15 except for the adhesive which is used to create the laminated sheet 130. In this embodiment, a wet bonding adhesive is used which does not require a drying tunnel. The shield forming sheet 70 has a full coating of adhesive applied thereto and the handle forming sheet 88 has adhesive applied in zones as described above. The shield forming sheet 70, handle forming sheet 88 and base material sheet 128 are rolled together to create the laminated sheet 130. The sheet can be transferred to a roll 132, transferred to a slitter 174 (FIG. 15) or transferred directly to the die cutter 165 (FIG. 15) for cutting the laminated sheet into individual laminated pads 12.

The fourth embodiment of the method for manufacturing a laminated pad according to the invention as seen in FIG. 18 can be modified to use pressure sensitive adhesive. For example, a full coating of adhesive can be applied to the shield forming sheet 70 and strips for zones of pressure sensitive adhesive can be applied to the handle forming sheet 88. The shield forming sheet 70, handle forming sheet 88 and base material sheet 128 are then rolled together to create the laminated sheet 130. As described above, the laminated sheet 130 can then be silt, rolled and die cut to create the individual laminated pads.

Figure 19:
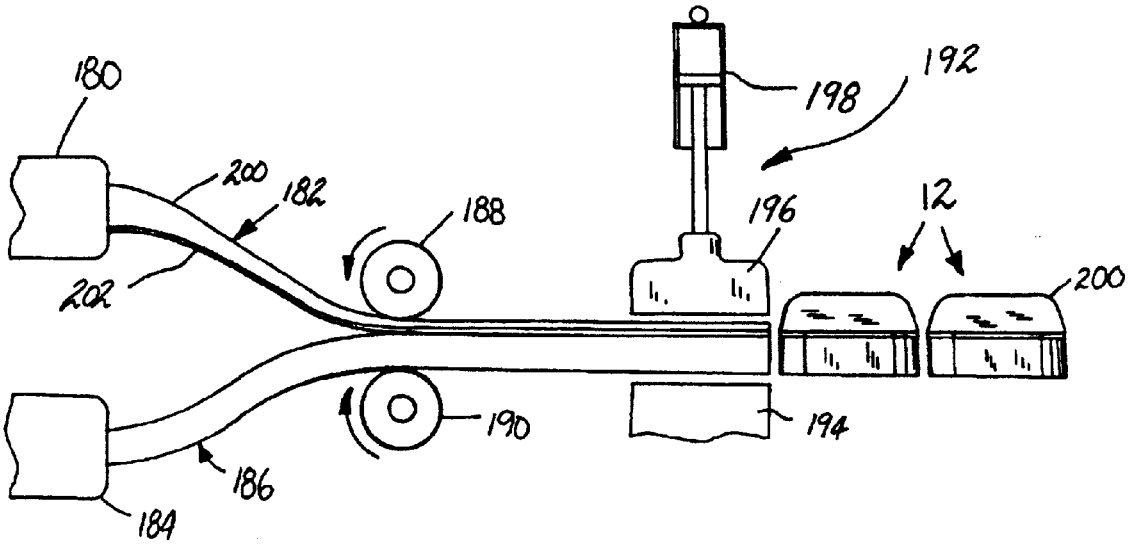
FIG. 19 is a schematic illustration of a fifth method of manufacturing the laminated pad according to the invention.

A fifth embodiment of the method for manufacturing a laminated pad according to the invention is seen in FIG. 19. In this embodiment, a first extruder 180 extrudes a member 182 which has an inverted T-shaped cross section and can be formed of a thin flexible plastic material having a thickness of approximately 2.5 millimeters. An adjacent second extruder 184 or dispenser provides a continuous elongated member 186 of a suitable base pad material. The extruded members 182, 186 are fed through a pair of opposed rollers 188, 190 that are rotated in the dictions indicated by their respective arrows. The rollers 188, 190 bring the two members 182, 186 together at the meeting surfaces and bond them into a combined, unitary structure. This unitary structure proceeds forward toward a conventional die cutting apparatus 192. The die cutter 192 comprises a back-up mandrel 194 which is disposed below a reciprocating cutter 196 powered by a suitable hydraulic or air cylinder 198.

Figure 20:
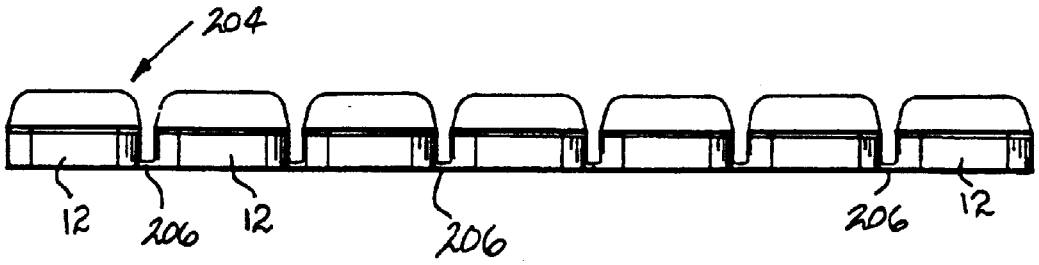
FIG. 20 is a side elevational view of an array of laminated pads produced according to the sixth embodiment of the method of manufacturing as seen in FIG. 19.

The upper roller 188 biases a central leg 200 of the T-shaped member 182 downward in a planar position parallel to the shield member 202 and the cutter 196 simultaneously cuts the members 182, 186. As the cuter 196 is removed, the centre leg or handle 200 will pop up to its upstanding position. The cutter 196 can be designed to cut the laminate into individual pads 12 or as illustrated in FIG. 20 can be aligned to only partially cut the array 204 of pads. In this case, the adjacent pads 12 are joined to one another by a web 206. The array of pads can be rolled into a roll or the like and dispensed by tearing off individual laminated pads from the array 204. In an embodiment that is not illustrated, the array 204 can have a number of rows and columns of laminated pads 12. Alternatively, a number of arrays 204 can be stacked and boxed in a nest-like fashion. A laminated pad is selected for use and the web 206 is torn, separating the selected pad 12 from the array 204. In an alternative embodiment that is not illustrated, the web 206 is formed from the shield or handle.

Figure 22:
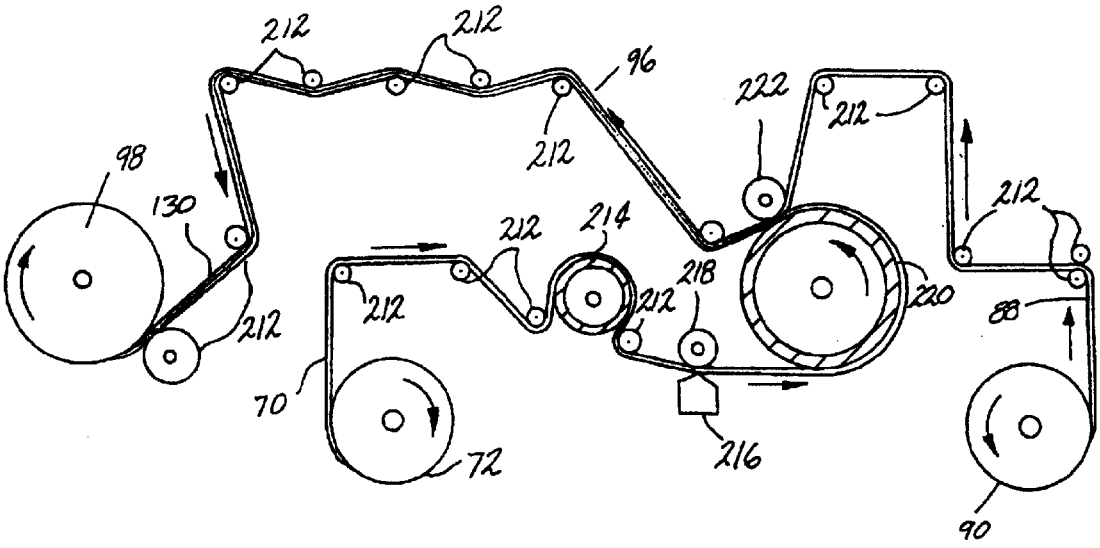
FIG. 22 is a schematic illustration of a sixth embodiment of a method for manufacturing a laminated pad according to the invention.

FIG. 22 depicts a sixth embodiment for manufacturing a laminated pad according to the invention. In this embodiment, the laminated sheet 130 is created by a hot melt adhesive bonding process. A sheet of shield forming material 70 is supplied on a roll 72 and the sheet 70 engages a plurality of guide rollers 212. Next, the sheet 70 engages a pre-heating roller 214 which heats the sheet 70. The sheet 70 then passes between a slot coater 216 and an opposed nip roller 218. The slot coater 216 applies hot adhesive to one side of the sheet 70. The adhesive is applied in longitudinal strips as depicted in FIGS. 13, 14 and 21. The coated sheet 70 then engages a chill drum 220 which cools both the sheet and the hot adhesive mounted thereto.

A sheet of handle forming material 88 is supplied from a roll 90. The sheet 88 engages several guide rollers 212 and is mounted to the adhesive-coated surface of the shield-forming sheet 70 by passing between a nip roller 222 and the chill drum 220 resulting in the creation of the laminated sheet 96. The laminated sheet 96 engages several guide rollers 212 and ultimately wound on a roll 98 for further processing. This same process can be used to mount the base-forming sheet 128 to the laminated sheet 96 by using a full coating gravure cylinder which applies adhesive along the full width of the base-forming sheet 128.

Figure 23:
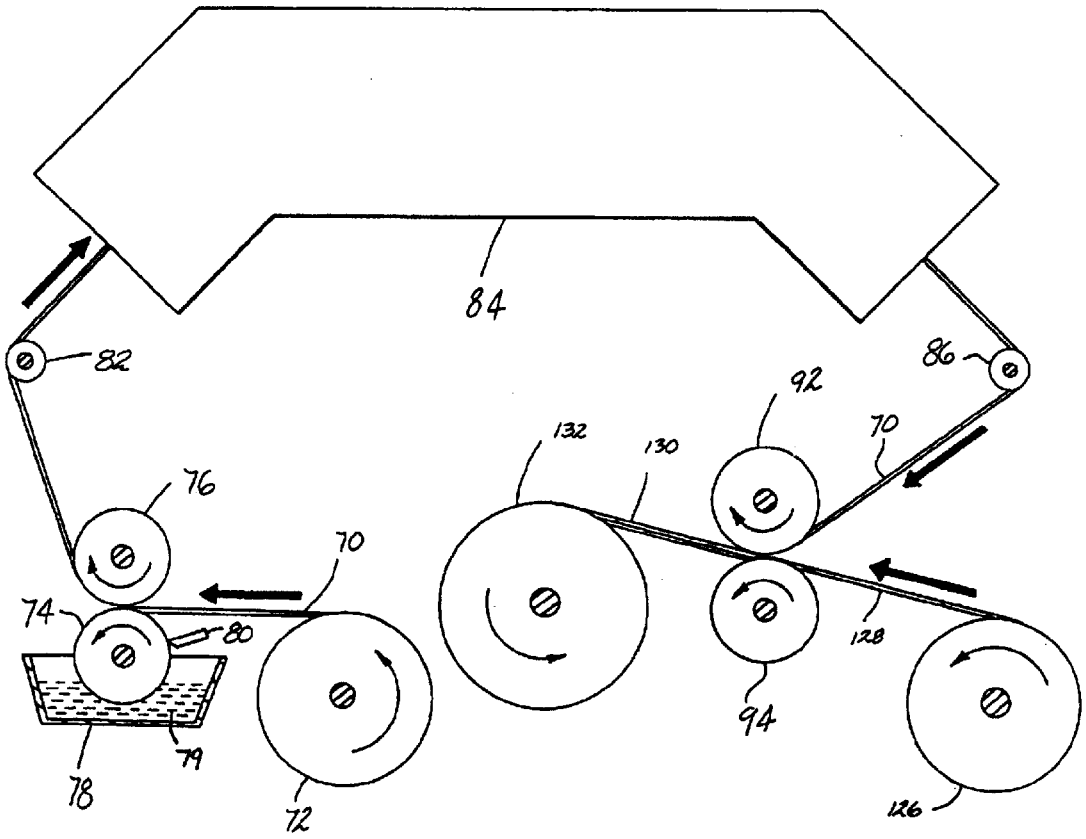
FIG. 23 is a schematic illustration of a seventh embodiment of a method for manufacturing a laminated pad according to the invention.

FIG. 23 shows a seventh embodiment of the method for manufacturing a laminated pad according to the invention. In this embodiment, the laminated sheet 130 is formed solely from a sheet of handle forming material 70 and abase pad sheet 128 wherein only a portion of the handle forming sheet is adhered to the base pad sheet through the selective application of longitudinal strips as depicted in FIG. 14. In this embodiment, the gravure roller 74 applies strips of adhesive to the attachment surface of the sheet of handle forming material 70 in the same manner as described above with respect to FIG. 5. Ultimately, the strips of adhesive on the sheet of handle forming material 70 are brought into contact with the attachment surface of the sheet of base pad material 128 by passing through rollers 92, 94. The resulting structure is a laminated web 130 which can be cut into individual pads as described above. However, these pads will comprise only a base pad and a handle. The only difference between this embodiment and the earlier embodiments is that the shield of impervious material has been deleted from this embodiment of the laminated pad.

While the embodiment described shove provides for application of the adhesive to the attachment surface of the sheet of handle forming material, it is to be understood that base pad material.

The laminated pad produced according to the invention can be used for the application of various materials such as liquids, pastes, powders, and the like to various surfaces and may be utilized for the removal of such materials. In addition, the laminated pad can be impregnated with a material to be applied. The laminated pad has unlimited uses in the medical field such as an absorbent applicator pad or wipe and in the cosmetic field for removing nail polish by the application of acetone and other solvents. The pad may also be used for the application and/or removal of facial and other skin cleansers, moisturizers, make-up, and tanning cream. The pad can also be used in the medical field for the application of various medications, applying cleaning solutions to a patient or absorbing fluids from a patient. The pad can be packaged and sterilized for these medical uses.

The method of manufacturing the pad according to the invention allows for the mass production of pads at a relatively low cost. Because the pads are produced from a single laminated sheet having zones of adhesive, the pads can be easily die cut and packaged.

While we have illustrated and described our invention by means of specific embodiments, it is to be understood that numerous changes and modifications may be made therein without departing from the spirit and scope of the invention as defined in the appended claims.

We claim:

1. A method of manufacturing a plurality of multilayer pads comprising the steps of:

providing a web of base pad forming material having a longitudinal axis, an attachment surface, an application surface and a prescribed [base pad] width; providing a web of intermediate layer forming material having a longitudinal axis, an upper attachment surface and a lower attachment surface;

providing a web of handle forming material having a longitudinal axis, a lower attachment surface, an exposed upper surface and a width substantially equal to the [base pad] *prescribed* width *of the web of base pad forming material*;

mounting the attachment surface of the base pad forming material to the lower attachment surface of the intermediate layer forming material so that substantially the entire lower attachment surface of the intermediate layer forming material is mounted [m] *to* the upper attachment surface of the base *pad* forming material;

applying [a strip] *strips* of adhesive to a portion of one of the upper attachment surface of the intermediate layer forming material and the lower attachment surface of the handle forming material along a longitudinal axis of said one surface;

mounting the upper attachment surface of the intermediate layer forming material to the lower attachment surface of the handle forming material so that the upper attachment surface of the intermediate layer forming material is adhered to the lower attachment at surface of the handle forming *material* along said strips of adhesive; and simultaneously cutting the base pad forming material, intermediate layer forming material and handle forming material to create at least two laterally adjacent multilayer pads having a base pad, an intermediate layer and a handle, the handle comprising a mounted portion and a pivotable portion[, wherein the mounted portion of the two pads are cut from the same strip of adhesive applied to said one of the handle forming material and the intermediate layer forming material].

2. A method of manufacturing a plurality of multilayer pads according to claim 1 and further comprising the step of scoring the web of the handle forming material between the mounted portion and the pivotable portion.

3. A method of manufacturing a plurality multilayer pads according to claim 1 wherein the base pad material is mounted to the intermediate layer by adhesive.

4. A method of manufacturing a plurality of multilayer pads according to claim 1 and further comprising the steps of providing a zone cylinder for applying the strip of adhesive to said one of the intermediate layer forming material and the handle forming material and rolling said one material over the zone cylinder, the zone cylinder having an adhesive applying portion and a smooth portion wherein the adhesive applying portion conveys adhesive from the cylinder to said one material and the smooth portion does not convey adhesive to said one material.

5. A method of manufacturing a plurality of multilayer pads according to claim 4 wherein said adhesive applying portion of the zone cylinder comprises a plurality of recesses formed thereon, the recesses conveying adhesive from a source of adhesive to the one material.

6. A method of manufacturing a plurality of multilayer pads according to claim 5 and further comprising the step of applying multiple strips of adhesive to a portion of one of the upper attachment surface of the intermediate layer forming material and the lower attachment, surface of the handle forming material along a longitudinal axis of said one surface wherein the surface of the zone cylinder further comprises an alternating sequence along the length of the cylinder of adhesive applying plurality of recesses and smooth portions resulting in the creation of said strips of adhesive on said one material corresponding to the recesses and smooth portions.

[7. A method of manufacturing a plurality of multilayer pads comprising the steps of:

providing a sheet of base pad forming material having a prescribed width, an attachment surface and an application surface;

providing a sheet of handle forming material having a width substantially equal to the base pad width, a lower attachment surface and an exposed upper surface;

applying at least two strips of adhesive to at least one of the attachment surface of the base pad and the lower attachment surface of the sheet of handle forming material;

selectively mounting a portion of the attachment surface of the base pad forming material to the lower attachment surface of the handle forming material such that less than the entire attachment surface of the base pad forming material is mounted to the lower attachment surface of the handle forming material; and cutting the laminated sheet into at least four individual pads aligned linearly in a direction substantially normal to the at least two strips of adhesive such that two laterally adjacent pads are cut from each strip of adhesive and the handle forming material of each pad comprises a mounted portion which is mounted to the base pad material and a pivotable portion which is not mounted to the base pad material.]

[8. A method of manufacturing a plurality of multilayer pads according to claim 7 wherein said at least two strips of adhesive are applied to the lower attachment surface of the sheet of handle forming material and further comprising the steps of:

providing a sheet of an intermediate layer forming material having an upper attachment surface and a lower attachment surface;

mounting the attachment surface of the base pad sheet to the lower attachment surface of the intermediate layer sheet such that substantially the entire lower attachment surface of the intermediate layer sheet is mounted to the upper attachment surface of the base pad sheet;

selectively mounting a portion of the upper attachment surface of the intermediate layer sheet and the lower attachment surface of the handle forming sheet to the other of the upper attachment surface of the intermediate layer sheet and the lower attachment surface of the handle forming sheet creating a laminated sheet such that less than the entire upper attachment surface of the intermediate layer forming sheet is mounted to the lower attachment surface of the handle forming sheet; and cutting the laminated sheet into at least four individual pads aligned linearly in a direction substantially normal to the at least two strips of adhesive such that two laterally adjacent pads are cut from each strip of adhesive and the handle forming material of each pad comprises a mounted portion which is mounted to the intermediate layer and a pivotable portion which is not mounted to the intermediate layer.]

[9. A method of manufacturing a plurality of multilayer pads according to claim 8 and further comprising the step of scoring the handle forming sheet at the junction of the mounted portion and the pivotable portion.]

[10. A method of manufacturing a plurality of multilayer pads according to claim 8 wherein the at least two strips of adhesive are applied to one of the intermediate layer forming sheet and the handle forming sheet by rolling said one sheet over a zone cylinder adapted to apply adhesive to the one sheet in said at least two strips.]

[11. A method of manufacturing a plurality of multilayer pads according to claim 10 wherein at least a portion of the surface of the zone cylinder has a plurality of recesses formed thereon, the recesses being adapted to convey adhesive from a source of adhesive to the one sheet.]

[12. A method of manufacturing a plurality of multilayer pads according to claim 11 and further comprising the step of passing the handle forming sheet and the intermediate layer sheet between a pair of opposed rollers so that said strips of adhesive provided on said one sheet contacts the other of the attachment surface of the handle forming sheet and the upper attachment surface of the intermediate layer sheet as the sheets pass between the opposed rollers.]

[13. A method of manufacturing a plurality of multilayer pads according to claim 11 wherein the surface of the zone cylinder comprises an alternating sequence along the length of the cylinder of the portion of recesses and a smooth portion resulting in the creation of strips of adhesive coating on the laminated sheet corresponding to the portion of recesses and strips of uncoated portions on the laminated sheet corresponding to the smooth portions.]

[14. A method of manufacturing a plurality of multilayer pads according to claim 13 and further comprising the step of cutting the laminated sheet such that the pivotable portion of two adjacent pads are cut from the same strip of uncoated portions of the laminated sheet.]

[15. A method of manufacturing a plurality of multilayer to claim 11 wherein the base material sheet is mounted to the intermediate layer sheet by an adhesive coating which is applied to one of the attachment surface of the base material sheet and the lower attachment surface of the intermediate layer sheet by rolling said one sheet over a cylinder having a plurality of recesses formed on the surface of the cylinder, the recesses being adapted to receive adhesive from a source of adhesive and transfer the adhesive to the sheet upon contact with the sheet.]

[16. A method of manufacturing a plurality of multilayer pads according to claim 15 and further comprising the step of drying the adhesive by subjecting the adhesive to a source of heat.]

[17. A method of manufacturing a plurality of multilayer pads according to claim 15 and further comprising the step of passing the base pad sheet and the intermediate layer sheet between a pair of opposed rollers such that the adhesive coated surface of said one sheet contacts the other of the attachment surface of the base material sheet and the lower attachment surface of the intermediate layer sheet.]

[18. A method of manufacturing a plurality of multilayer pads according to claim 7 and further comprising the step of cutting the laminated sheet so that the laminated pad has at least one arcuate edge and at least one straight edge.]

*19. A method of manufacturing a plurality of multilayer pads comprising the stems of:*

*providing a web of base pad forming material having a longitudinal axis, a width, an attachment surface and an application surface;*

*providing a web of intermediate layer forming material having a longitudinal axis, a width, an upper attachment surface and a lower attachment surface;*

*providing a web of handle forming material having a longitudinal axis, a width, a lower attachment surface and an exposed upper surface;*

*applying longitudinally continuous and laterally spaced strips of adhesive to portions of one of the upper attachment surface of the intermediate layer forming material and the lower attachment surface of the handle forming material along the longitudinal axis of the one surface;*

*mounting the attachment surface of the base pad forming material to the lower attachment surface of the intermediate layer forming material so that the lower attachment surface of the intermediate layer forming material is mounted to the upper attachment surface of the base pad forming material over the widths of the webs of base pad forming material and intermediate layer forming material, and mounting the upper attachment surface of the intermediate layer forming material to the lower attachment surface of the handle forming material so that the upper attachment surface of the intermediate layer forming material and the lower attachment surface of the handle forming material are adhered to each other along the laterally spaced strips of adhesive to produce a laminated sheet; and*

*cutting the laminated sheet to produce individual multilayer pads each having a base pad, an intermediate layer and a handle, the cutting being such that the handle of each multilayer pad has a mounted portion adhered to the intermediate layer where adhesive was applied and a pivotable portion.*

* * * * *